(12) United States Patent
Small et al.

(10) Patent No.: US 12,422,421 B2
(45) Date of Patent: *Sep. 23, 2025

(54) LOW POWER MIXED GAS SENSOR

(71) Applicant: National Technology & Engineering Solutions of Sandia, LLC, Albuquerque, NM (US)

(72) Inventors: Leo J. Small, Albuquerque, NM (US); Stephen J. Percival, Albuquerque, NM (US); Tina M. Nenoff, Albuquerque, NM (US); Mara E. Schindelholz, Columbus, OH (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 311 days.

This patent is subject to a terminal disclaimer.

(21) Appl. No.: 18/103,617

(22) Filed: Jan. 31, 2023

(65) Prior Publication Data
US 2023/0168231 A1   Jun. 1, 2023

Related U.S. Application Data

(63) Continuation-in-part of application No. 17/173,333, filed on Feb. 11, 2021, now Pat. No. 11,573,217.

(51) Int. Cl.
*G01N 33/00* (2006.01)
*G01N 27/12* (2006.01)
*G01N 27/22* (2006.01)

(52) U.S. Cl.
CPC ......... *G01N 33/0027* (2013.01); *G01N 27/12* (2013.01); *G01N 27/227* (2013.01)

(58) Field of Classification Search
CPC .. G01N 33/0027; G01N 27/12; G01N 27/227; G01N 27/026; G01N 33/0031;
(Continued)

(56) References Cited

U.S. PATENT DOCUMENTS

2010/0139365 A1   6/2010   Fix et al.
2019/0302078 A1*  10/2019  Small ............... G01N 27/125
(Continued)

OTHER PUBLICATIONS

Chernikova, Valeriya, et al. "Highly sensitive and selective SO 2 MOF sensor: the integration of MFM-300 MOF as a sensitive layer on a capacitive interdigitated electrode." Journal of Materials Chemistry A 6.14 (2018): 5550-5554. (Year: 2018).*
(Continued)

*Primary Examiner* — Timothy P Graves
(74) *Attorney, Agent, or Firm* — Kevin W. Bieg

(57) ABSTRACT

The invention is directed to a chemically robust, highly-selective, low power sensor that can be used for the direct electrical detection of mixed gases. In particular, metal-organic frameworks (MOFs) offer exceptional chemical and structural tunability as mixed-gas capture materials. As an example of the invention, the influence of interfering gases on trace $NO_2$ detection in a simulated flue gas stream was investigated. The unique interaction of $NO_2$ with the MOF's metal center leads to orders of magnitude decrease in MOF resistance. More broadly, the coadsorption of specific gases (e.g., $H_2O$, $SO_2$) can be beneficial to the electrical detection of the target gas (e.g., $NO_2$), and careful electrical measurements can discern their presence independent of the target gas.

11 Claims, 7 Drawing Sheets

(58) Field of Classification Search
CPC ............. G01N 33/0037; G01N 33/004; G01N 33/0047; Y02A 50/20
See application file for complete search history.

(56) References Cited

U.S. PATENT DOCUMENTS

2019/0339227 A1* 11/2019 Drmosh .................. C23C 14/16
2021/0231628 A1    7/2021 Nenoff et al.

OTHER PUBLICATIONS

Chernikova, V. eta I., "Highly sensitive and selective So2 MOF sensor: the integration of MFM-300 MOF as a sensitive layer on a capacitive interdigitated electrodes," Journal of Materials Chemistry A (2018) 6:5550-5554.

De Oliveira, A. et al., "Structural and electronic properties of M-MOF-74 (M=MG, CO OR MN)," Chemical Physics Letters (2018) 691:283-290.

Percival, S. J. et al., "Nickel-Loaded SSZ-13 Zeolite-Based Sensor for the Direct Electrical Readout Detection of NO2," Ind. Eng. Chem. Res. (2021) 60:14371-14380.

Small, L. J. et al., "Direct Electrical Detection of Iodine Gas by a Novel Metal-Organic-Framework-Based Sensor," ACS Appl. Mater. Interfaces (2017) 9:44649-44655.

Small, L. J. et al., "Reversible MOF-Based Sensors for the Electrical Detection of Iodine Gas," ACS Appl. Mater. Interfaces (2019) 11:27982-27988.

Small, L. J. et al., "Near-Zero Power MOF-Based Sensors for NO2 Detection," Adv. Funct. Mater. (2020) 30:2006598, 8 pages.

Tan, K. et al., "Competitive Coadsorption of CO2 with H2O, NH3, SO2, NO, NO2, N2, O2, and CH4 in M-MOF-74 (M=Mg, Co, Ni): The Role of Hydrogen Bonding," Chemistry of Materials (2015) 27:2203-2217.

Tan, K. et al., "Interaction of Acid Gases SO2 and NO2 with Coordinatively Unsaturated Metal Organic Frameworks: M-MOF-74 (M=Zn, Mg, Ni, Co)," Chemistry of Materials (2017) 29:4227-4235.

* cited by examiner

LOW POWER MIXED GAS SENSOR

CROSS-REFERENCE TO RELATED APPLICATION

This application is a continuation-in-part of U.S. application Ser. No. 17/173,333, filed Feb. 11, 2021, which is incorporated herein by reference.

STATEMENT OF GOVERNMENT INTEREST

This invention was made with Government support under Contract No. DE-NA0003525 awarded by the United States Department of Energy/National Nuclear Security Administration. The Government has certain rights in the invention.

FIELD OF THE INVENTION

The present invention relates to gas sensing and, in particular, to a low power mixed gas sensor that can detect individual gases in mixed gas streams.

BACKGROUND OF THE INVENTION

Selective gas sensors with long lifetimes, low power consumption, and high chemical durability are needed for myriad of applications, ranging from environmental monitoring to removing toxic gases from industrial waste streams. See M. A. A. Mamun and M. R. Yuce, *IEEE Sensors J.* 19, 7771 (2019); and A. Kaushik et al., *Chem. Rev.* 115, 4571 (2015). Toxic acid gases present in flue gas streams are of particular importance, where multiple toxic gases such as $SO_x$ and $NO_x$ are present. See F. Rezaei et al., *Energy Fuels* 29, 5467 (2015); and H. Wang et al., *Chem. Eng. J.* 378, 122155 (2019).

Metal-organic frameworks (MOFs) are a highly tunable class of materials uniquely suited to meet this challenge. See L. E. Kreno et al., *Chem. Rev.* 112, 1105 (2012); L. J. Small et al., *Ind. Eng. Chem. Res.* 60, 7998 (2021); A. J. Rieth et al., *Nat. Rev. Mat.* 4, 708 (2019); I. Stassen et al., *ACS Cent. Sci.* 5, 1425 (2019); L.-T. Zhang et al., *Angew. Chem. Int. Ed.* 60, 15192 (2020); and H.-Y. Li et al., *Chem. Soc. Rev.* 49, 6364 (2020). Indeed, the scientific community has recognized this opportunity and many groups have reported using MOFs as gas sensors for $H_2S$, $CO_2$, $SO_2$, $NO_2$, among other acid gases. See M. K. Smith et al., *Chem. Mater.* 28, 5264 (2016); E. Martinez-Ahumada et al., *Organometallics* 39, 883 (2020); I. Stassen et al., *ACS Cent. Sci.* 5, 1425 (2019); S. Achmann et al., *Sensors* 9, 1574 (2009); I. Strauss et al., *ACS Appl. Mater. Interfaces* 11, 14175 (2019); K.-J. Kim et al., *ACS Appl. Mater. Interfaces* 13, 2062 (2021); V. Chernikova et al., *J. Mater. Chem. A.* 6, 5550 (2018); M. Wang et al., *Anal. Chem.* 90, 3608 (2018); X. Zhang et al., *Chem. Nano Mat.* 7, 1117 (2021); L. J. Small et al., *Adv. Funct. Mater.* 30, 2006598 (2020); S. J. Percival et al., *Ind. Eng. Chem. Res.* 60, 14371 (2021); M. Schulz et al., *Angew. Chem. Int. Ed.* 57, 12961 (2018); C. Arul et al., *Sens. Actuators B: Chem.* 329, 129053 (2021); M. Zhan et al., *Mater. Res. Bull.* 136, 11133 (2021); M. W. Khan et al., *J. Colloid Interface Sci.* 610, 304 (2022); and J. Zhang et al., *Mater. Chem. Front.* 5, 6476 (2021). The adsorption of the target gas by the MOF may be transduced by a variety of mechanisms, including changes in MOF mass, optical properties, and electrical properties. See K.-J. Kim et al., *ACS Appl. Mater. Interfaces* 13, 2062 (2021); I. Sasaki et al., *Sens. Actuators B* 86, 26 (2002); J. R. Alvarez et al., *Inorg. Chem. Front.* 2, 1080 (2015); M. R. Tchalala et al., *Nat. Commun.* 10, 1 (2019); M. Wang et al., *Anal. Chem.* 90, 3608 (2018); D. Ma et al., *Chem. Commun.* 49, 8964 (2013); D. F. S. Gallis et al., *ACS Appl. Mater. Interfaces* 11, 43270 (2019); S. Achmann et al., *Sensors* 9, 1574 (2009); X. Zhang et al., *Chem. Nano Mat.* 7, 1117 (2021); L. J. Small et al., *Adv. Funct. Mater.* 30, 2006598 (2020); S. J. Percival et al., *Ind. Eng. Chem. Res.* 60, 14371 (2021); Y.-M. Jo et al., *Adv. Mater.*, e2206842 (2022); and S. M. Majhi et al., *Nano Energy* 79, 105369 (2021). In particular, changes in electrical properties are of interest for simplicity and ease of integration into low-cost electronics.

SUMMARY OF THE INVENTION

The invention is directed to a low power mixed gas sensor, comprising an electrically insulating substrate; a pair of interdigitated electrodes disposed on the substrate; a mixed-gas-capture film disposed on the pair of interdigitated electrodes and the substrate; and a frequency response analyzer for measuring the impedance response of the mixed-gas-capture film when a mixed gas steam is absorbed in the mixed-gas-capture film and an alternating voltage is applied to the pair of interdigitated electrodes. The mixed-gas-capture film can comprise a metal organic-framework (MOF) material, such as M-MOF-74, where M is cobalt, magnesium, zinc, or nickel, or RE-DOBDC, where RE is a rare-earth element and DOBDC is dihydroxyterephthalic acid. The frequency can correspond to a RC transition frequency that leverages the capacitive component of the MOF to increase the signal strength while still enabling a larger signal change associated with the DC resistance to be calculated. A high impedance interface can be connected in series with the frequency response analyzer.

The invention is further directed to a method for detecting individual gases in a mixed gas stream, comprising providing a low power mixed gas sensor, exposing the mixed gas sensor to a mixed gas stream; and measuring the impedance response of the mixed-gas-capture film.

As an example of the invention, the impedance response of Ni-MOF-74 was systematically evaluated at 50° C. under 16 unique combinations of $N_2$, $NO_2$, $SO_2$, and $CO_2$ under both dry and humid (0.8% $H_2O$) conditions. Through this analysis it is seen that $NO_2$ drives the large (up to 6060×) change in $R_{MOF}$. This change in $R_{MOF}$ occurs by two electrically distinct processes, one fast and one slower. $CO_2$ inhibits $NO_2$ adsorption, specifically the faster adsorption process, though this effect can be reversed by adding $SO_2$. The adsorption of $H_2O$ by Ni-MOF-74 is rapid (<120 s), much faster than $NO_2$. Moreover, co-adsorption of competing gases under humid conditions enhances the change in $R_{MOF}$. Together, these results suggest that coadsorption of specific gases (e.g., $H_2O$, $SO_2$) can be beneficial to the electrical detection of the target gases ($NO_2$), and that careful electrical measurements can even discern their presence independent of the target gas. Thus, to enhance the overall electrical response, it is not necessary for the MOF to be 100% selective for a given gas species; intentionally designing the MOF to accept complementary gases can be beneficial.

BRIEF DESCRIPTION OF THE DRAWINGS

The detailed description will refer to the following drawings, wherein like elements are referred to by like numbers.

FIG. 7A is a graph of impedance magnitude (|Z|) over time under dry conditions. Data have been normalized to the initial measurement ($|Z|_0$). FIG. 7B is a graph showing linearization of the data in FIG. 7A. FIG. 7C is a graph of |Z| over time for humid test conditions. This graph has been zoomed in on the first hour to reveal key differences induced by humidity ($H_2O$).

DETAILED DESCRIPTION OF THE INVENTION

Key attributes for long-lived, near-zero power chemical sensors include: (1) extremely high resistance (>$10^9 \Omega$) in the activated state, (2) strong active material-analyte binding to prevent escape of captured analytes, and (3) large per-unit-cell adsorption capacity coupled with (4) a favorable redox potential of the analyte with respect to the active capture material. These characteristics enable a low power sensor with irreversible analyte capture and a corresponding large change in sensor electrical response.

Figure 1A:
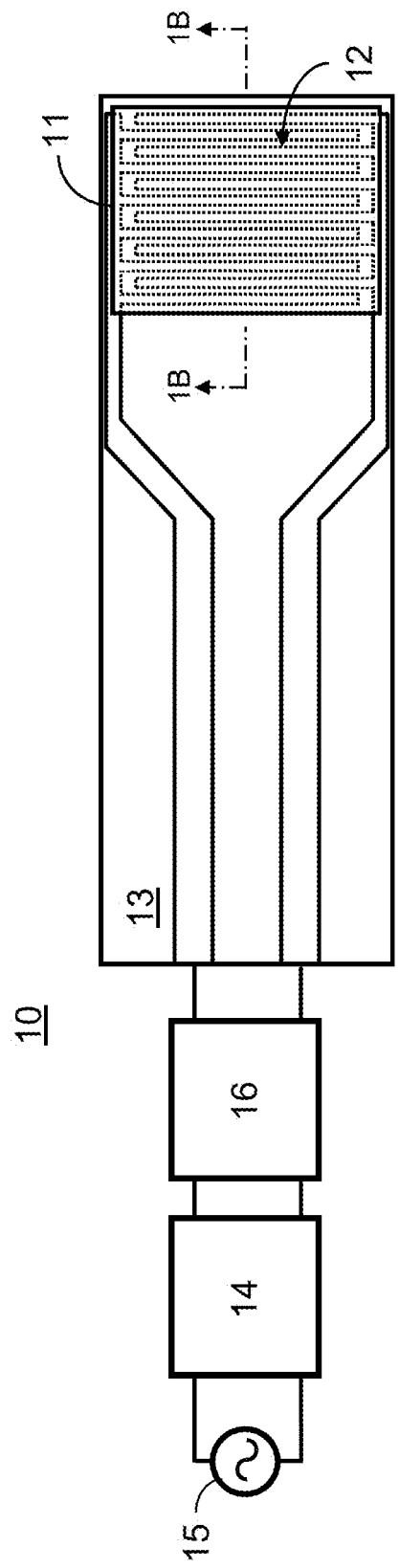
FIG. 1A is a top-view schematic illustration of a low power sensor for the direct electrical detection of a mixed gas stream.
Figure 1B:
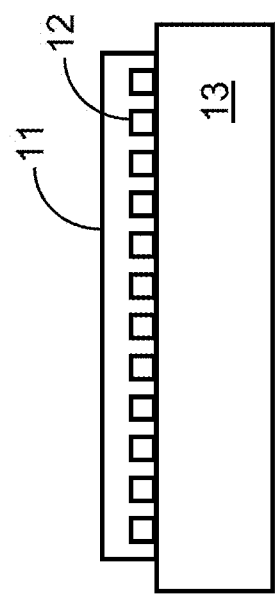
FIG. 1B is a cross-sectional side-view schematic illustration of the mixed gas sensing region of the sensor.

As shown in FIGS. 1A and 1B, the low power mixed gas sensor 10 comprises a mixed-gas-capture film 11 disposed on interdigitated electrodes (IDEs) 12. The mixed-gas-capture material is preferably a metal-organic framework (MOF) or a microporous aluminosilicate (zeolite). The IDEs 12 comprise a pair of interlocking comb-shaped arrays of metallic electrodes deposited on the surface of an electrically insulating substrate 13. The substrate is preferably more electrically insulating (i.e., has a higher resistivity) than the mixed-gas-capture material. For example, the substrate can be a high resistance silica glass.

A variety of analyzers can be used to detect changes in electrical properties of the mixed-gas-capture material when exposed to a mixed-gas stream. For example, impedance spectroscopy can be used to measure the electrical impedance of the coated IDEs over a range of frequencies. Therefore, the sensor 10 can further comprise a frequency response analyzer 14 for measuring the impedance response of the mixed-gas capture film when an AC voltage 15 is applied to the IDEs 12. In materials where the dielectric loss is very small and the permittivity is large, a high impedance interface 16 can be connected in series with the frequency response analyzer 14 to provide a more accurate impedance measurement.

Mixed-Gas-Capture Materials

A well-known family of MOFs, MOF-74, has been extensively studied for the interaction of the metal center with different acid gases, such as $NO_x$, $SO_x$, $CO_2$, and $H_2O$, and the competitive binding of each investigated by both computational and experimental methods. See K. Tan et al., *Chem. Mater.* 29, 4227 (2017). M-MOF-74 are a series of isostructures with a variety of metals (M=Mg, Ni, Co, Zn) and the same organic ligand, 2,5-dihydroxyterephthalic acid (DHTP). Current literature has highlighted the uniqueness of electronic structure in M-MOF-74 as a function of metal choice and response to various adsorbed gases. See A. de Oliveira et al., *Chem. Phys. Lett.* 691, 283 (2018); K. Tan et al., *Chem. Mater.* 27, 2203 (2015); and K. Tan et al., *Chem. Mater.* 29, 4227 (2017). Each adsorbed gas has been calculated to modify M-MOF-74 electronic structures to a varying degree, indicating the possibility for sensing of unique chemical species. For application in electrical sensing, the change in electronic structure, due to gas adsorption, modifies the effective masses of electrons and holes, therefore changing the conductivity of the MOF material.

In particular, Ni-MOF-74 is a promising candidate for these applications, having demonstrated large changes in electrical properties upon adsorption of dry $NO_2$. See L. J. Small et al., *Adv. Funct. Mater.* 30, 2006598 (2020). The performance under more industrially-relevant conditions, however, is not well known, where multiple competing gases ($H_2O$, $SO_2$, $CO_2$, etc.) may be present and coadsorb on the MOF. See L. Ding and A. O. Yazaydin, *J. Phys. Chem. C* 116, 22987 (2012). Detailed FT-IR studies by Tan et al. have shown complex competition between these gases in MOF-74, where kinetic limitations strongly influence exchange of adsorbed gases. See K. Tan et al., *Chem. Mater.* 27, 2203 (2015); and K. Tan et al., *Chem. Mater.* 29, 4227 (2017). It is worth noting that unlike gas detection via mass changes, using electrical properties to detect gas adsorption may result in conditions where gas is adsorbed, but not detected, if the adsorption of the gas does not influence the electronic structure of the MOF, or otherwise alter the electrical properties of the MOF film (e.g., surface conduction via adsorbed water along the MOF crystallite exterior). See L. Sun et al., *Chem. Sci.* 8, 4450 (2017).

Another MOF that can be used with the invention includes RE-DOBDCs (where RE is a rare earth element and DOBDC is dihydroxyterephthalic acid). These RE-DOBDC MOFs have recently been shown to have strong binding of $N_2O$ and $H_2O$ and have been used for the photoluminescence-based detection of acid gases, including $NO_x$. See Patent Appl. No. US 2021/0231628, which is incorporated herein by reference.

A number of microporous aluminosilicates (zeolites) are also suitable as mixed-gas-capture materials.

Frequency Response

Direct electrical detection of gaseous analytes by MOFs can be performed through either a change in the capacitance or resistance of the MOF-containing sensor. Changes in capacitance are typically measured by an alternating voltage at relatively high frequency (e.g., 1 MHz), such as the $SO_2$ sensor Chernikova et al. built to successfully detect ppb levels of $SO_2$. See V. Chernikova et al., *J. Mater. Chem. A*

6, 5550 (2018). Changes in capacitance for MOF-based sensors are typically small, however, as the change is based on the real permittivity of the MOF having adsorbed one gas (e.g., $N_2$) versus another (e.g., $SO_2$). On the other hand, changes in MOF resistance in response to a gaseous analyte are typically recorded as DC measurements, e.g., a chemiresistor. See I. Stassen et al., *ACS Cent. Sci.* 5, 1425 (2019); M. L. Aubrey et al., *J. Amer. Chem. Soc.* 141, 5005 (2019); and M.-S. Yao et al., *Angew. Chem. Int. Ed.* 58, 14915 (2019). While this approach offers potentially large changes in signal for the right MOF-analyte combinations, it can be technically challenging, as many MOFs possess resistivities approaching those of common insulators, such as alumina. See L. J. Small and T. M. Nenoff, *ACS Appl. Mater. Interfaces* 9, 44649 (2017); L. J. Small et al., *ACS Appl. Mater. Interfaces* 11, 27982 (2019); A. A. Talin et al., *Science* 343, 66 (2014); and L. Sun et al., *J. Amer. Chem. Soc.* 137, 6164 (2015). Therefore, many groups have worked towards identifying lower resistivity MOFs. See I. Stassen et al., *Chem. Soc. Rev.* 46, 3185 (2017); and S. K. Bhardwaj et al., *J. Mater. Chem. A* 6, 14992 (2018). A downside to decreasing the MOF resistivity, however, is an increase in the sensor's power consumption. While resistive components dissipate power, purely capacitive (e.g., reactive, or imaginary impedance) components do not. See E. Barsoukov and J. R. Macdonald, *Impedance Spectroscopy: Theory, Experiment, and Applications,* 2nd Ed., Wiley, Hoboken, NJ, USA (2005).

The impedance can be related to the capacitance and conductivity of the MOF material. When an alternating voltage is applied to the IDE, some energy is stored by the capacitance, and some is dissipated by the resistance effects. Therefore, the resulting current will exhibit a phase lag. The capacitance effect is known as the permittivity (or dielectric constant), and the resistive effect as dielectric loss. The sensor can be operated at an AC frequency corresponding to a RC transition frequency that leverages the capacitive component of the MOF material to increase the signal strength while still enabling the larger signal change associated with the DC resistance to be calculated. The high impedance interface enables a reference measurement to be obtained on precision internal reference capacitors which are automatically substituted for the sample; a second measurement is made, this time on the sample itself. The two results can be used to derive an accurate measurement of the permittivity of the MOF material—in effect, the first measurement is used to eliminate the effects of extraneous capacitance.

The present invention marries the high signal strength and low power consumption of a capacitive MOF sensor with the large signal change of a resistive MOF sensor. The invention uses a hybrid approach whereby impedance spectroscopy is first applied in the lab to understand the AC frequency response across a wide range (1 mHz-1 MHz), and then used to extrapolate the DC resistance of the mixed gas sensor. From this data, a single RC transition frequency (e.g., 100 mHz) is selected, leveraging the capacitive component of the MOF material to increase the signal strength while still receiving information about the MOF's DC resistance. With this hybrid approach, both the high resistivity and mixed gas selectivity of an exemplary Ni-MOF-74 was leveraged to create an active material for a near-zero power sensor which detects the presence of individual gases in a mixed gas stream through changes in the electrical properties of MOF-74.

As described in U.S. Pat. No. 11,573,217, a low power nitrogen oxide sensor has been developed that provides direct electrical detection of trace (0.5-5 ppm) $NO_2$ at relatively low temperatures (50° C.) via changes in the electrical properties of nitrogen-oxide-capture active materials. The high impedance of MOF-74 enables applications requiring a low power sensor, with 0.8 mg MOF-74 active material drawing <15 pW for a macroscale sensor 35 mm² area. As will be described below, this same sensor can be used to detect individual gases in mixed gas streams, for example comprising two or more of $NO_x$, $H_2O$, $SO_x$, and/or $CO_x$.

MOF-Based Mixed Gas Sensor Fabrication

A series of sensors were fabricated by dropcasting Ni-MOF-74 powders on IDEs on glass substrates. In order to evaluate the influence of the MOF-74 metal center on mixed gas sensing ability, a series of IDEs were coated with Ni-MOF-74, activated at 200° C. under vacuum, and interrogated with impedance spectroscopy at varying mixed gas compositions.

Ni-MOF-74 was synthesized using a literature procedure, with minor alterations. See S. M. Vornholt et al., *Dalton Trans.* 46, 8298 (2017); S. E. Henkelis et al., *Cryst. Eng. Commun.* 21, 1857 (2019); and L. J. Small et al., *Adv. Funct. Mater.* 2006598, 1 (2020). To synthesize Ni-MOF-74, nickel acetate tetrahydrate (1.24 g, 5.00 mmol) was dissolved in water (14 mL) with stirring. 2,5-dihydroxyterephthalic acid (0.5 g, 2.50 mmol) was dissolved in sodium hydroxide (1 M, 10 mL) and added dropwise to the salt solution in 1 mL aliquots over 5 mins. The reaction solution was heated to reflux for 16 hr and then allowed to cool. The powder was collected by filtration, washed with methanol (2×100 mL) and water (2×100 mL) and allowed to dry overnight in air. For use in the dropcast powder sensor, the Ni-MOF-74 were ground into a fine powder using a mortar and pestle.

Platinum IDEs on glass substrates were obtained from DropSens (product G-IDEPT10). These IDEs contain 125 pairs of platinum lines 250 nm thick and 10 µm wide with a spacing of 10 µm between lines. The IDEs were cleaned under $N_2$ flow, and their impedance magnitude at 100 mHz was verified to be greater than $3\times10^{10}\Omega$. In a 10 mL glass vial, 25 mg of the MOF-74 powder and 1 mL acetone were mixed. The mixture was sealed and stirred vigorously for 30 minutes, after which 12.5 µL was pipetted onto the active area of the IDE. The IDE was allowed to dry at room temperature for 5 mins, followed by deposition of another 12.5 µL of the MOF suspension. This resulted in 0.8 mg of MOF-74 being deposited on the active area of the IDE (~35 mm²). Film thickness of the dropcast powder coatings was determined to be on the order of 10 µm.

Mixed Gas Exposure and In-Situ Electrical Testing

Ni-MOF-74-coated IDEs were loaded into a custom-built gas exposure chamber that enabled MOF activation and subsequent in-situ electrical testing under varying gaseous environments without exposure to lab atmosphere. Impedance spectra were simultaneously recorded using either (1) a Solartron 1260 Frequency Response Analyzer connected in series with a Solartron 1296 Dielectric Interface or (2) a Solartron Modulab with both femtoammeter and reference measurement cards. Regardless of instrument, all measurements utilized the internal reference capacitors to increase measurement accuracy.

During the initial measurements when 1.5 h of pure $N_2$ was flowed, impedance spectra were recorded at 0 V DC and 100 mV (RMS) AC over 1 MHz to 10 mHz (10 points/ decade) for IDEs in three separate test slots. Afterwards, continuous measurements were recorded at 100 mHz for IDEs in one or two of the test slots. Measurements at 100 mHz continued until the gas mixture of interest had been flowed for 5 h. Impedance spectra over 1 MHz-10 mHz were then recorded for all IDEs. The chamber was opened, all three IDEs were immediately removed, and they were either (1) examined in Fourier transform infrared (FT-IR) spectroscopy, (2) interrogated in powder X-ray diffraction (PXRD), or (3) sealed in a glass vial for subsequent analysis at a synchrotron. All electrical measurements and gas exposures occurred at 50° C.

A study was conducted to determine the relation between competing gas composition, gas coadsorption in Ni-MOF-74, and resulting changes in electrical properties for Ni-MOF-74 when detecting trace $NO_2$. To understand how the competitive adsorption of $N_2$, $NO_2$, $SO_2$, $CO_2$, and $H_2O$ influences the ability of Ni-MOF-74-based gas sensors to electrically detect trace $NO_2$, a large batch of Ni-MOF-74 powder was synthesized, dropcast onto interdigitated electrodes, activated at 200° C. under vacuum, and exposed to different gas combinations at 50° C. Mimicking an industrial acid-gas stream, $N_2$ carrier gas was used to introduce $NO_2$ or $SO_2$ at 1 ppm, $CO_2$ at 10% (100,000 ppm), or $H_2O$ at 0.8% (8,000 ppm); all gas combinations are outlined in Table 1. MOF phase stability was verified via PXRD, while gas adsorption was confirmed via FT-IR. The sensor electrical response before, during, and after gas exposure was correlated to specific gas adsorption sites identified by differential electron density analysis.

TABLE 1

Compilation of the different gas combinations and corresponding concentrations.

| Gas Combination | Concentration of Individual Gases | | | | |
|---|---|---|---|---|---|
| | $N_2$/% | $NO_2$/ ppm | $SO_2$/ ppm | $CO_2$/ wt % | $H_2O$/ wt % |
| Dry conditions | | | | | |
| $N_2$ | 99.999 | 0 | 0 | 0 | 0 |
| $NO_2$ | balance | 1 | 0 | 0 | 0 |
| $SO_2$ | balance | 0 | 1 | 0 | 0 |
| $CO_2$ | balance | 0 | 0 | 10 | 0 |
| $NO_2 + SO_2$ | balance | 1 | 1 | 0 | 0 |
| $NO_2 + CO_2$ | balance | 1 | 0 | 10 | 0 |
| $SO_2 + CO_2$ | balance | 0 | 1 | 10 | 0 |
| $NO_2 + SO_2 + CO_2$ | balance | 1 | 1 | 10 | 0 |
| "Humid" Conditions | | | | | |
| $N_2$ | balance | 0 | 0 | 0 | 0.8 |
| $NO_2$ | balance | 1 | 0 | 0 | 0.8 |
| $SO_2$ | balance | 0 | 1 | 0 | 0.8 |
| $CO_2$ | balance | 0 | 0 | 10 | 1.6 |
| $NO_2 + SO_2$ | balance | 1 | 1 | 0 | 0.8 |
| $NO_2 + CO_2$ | balance | 1 | 0 | 10 | 0.8 |
| $SO_2 + CO_2$ | balance | 0 | 1 | 10 | 1.6 |
| $NO_2 + SO_2 + CO_2$ | balance | 1 | 1 | 10 | 0.8 |

Impedance Response to Mixed Gas Exposure

Figures 2A, 2B:
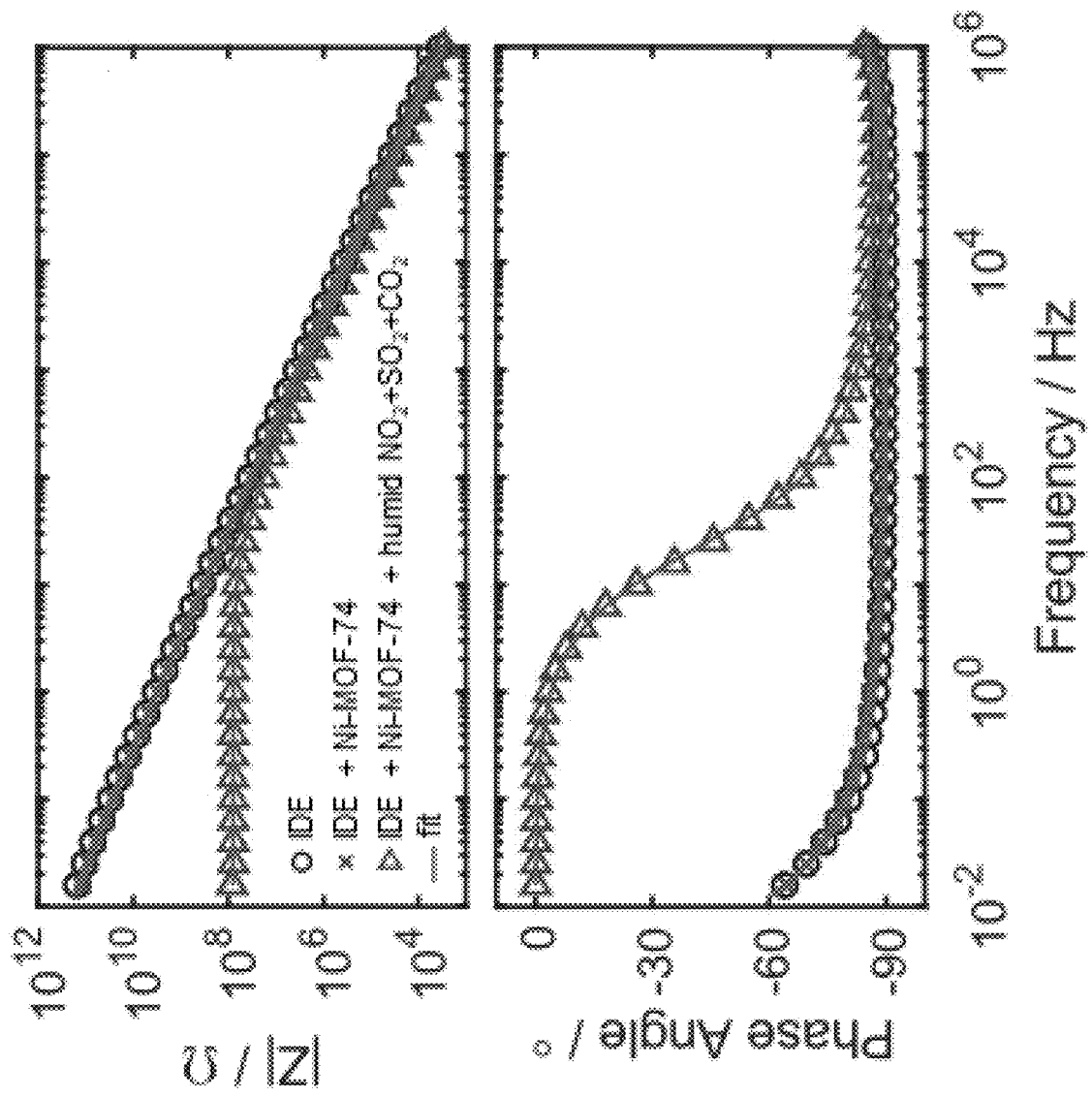
FIG. 2A is a graph of the impedance magnitude for a bare IDE, an IDE coated with activated Ni-MOF-74, and a Ni-MOF-74 coated IDE activated and then exposed to humid $NO_2+SO_2+CO_2$. For clarity, only every other datapoint is plotted.
FIG. 2B is a graph of the phase angle.
Figure 3:
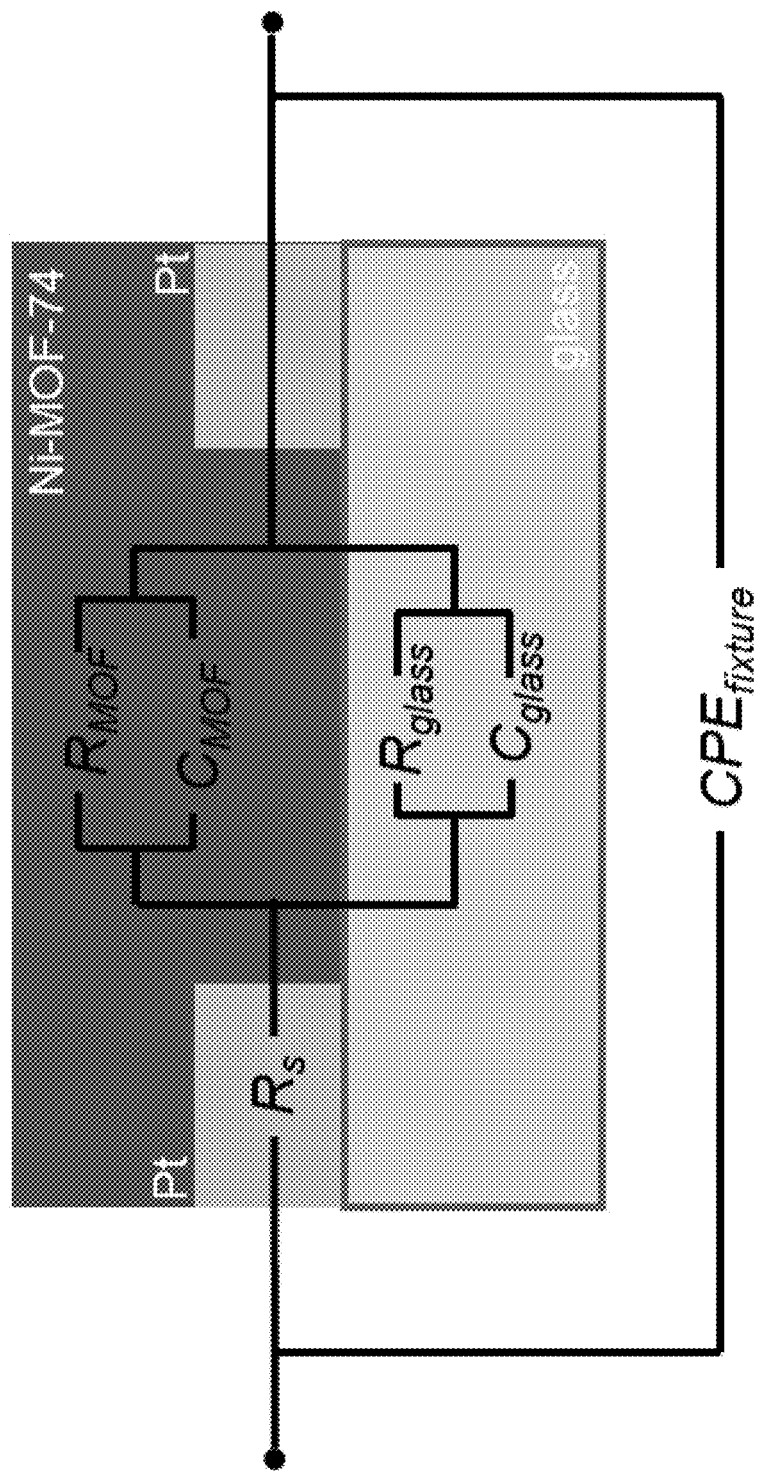
FIG. 3 shows an equivalent circuit used to fit experimental impedance data overlaid onto a schematic of the materials system. Here 'R' signifies a resistance and 'C' denotes a capacitor.

The impedance response of the Ni-MOF-74 coated IDEs were recorded before and after gas exposure; example spectra are provided in FIGS. 2A and 2B for exposure to humid $NO_2+SO_2+CO_2$. The bare IDE shows a highly capacitive response, with impedance magnitude (|Z|) displaying a straight line, and the phase angle residing near −90° except for very low frequencies <0.1 Hz. Addition of the activated Ni-MOF-74 retains most of this capacitive response, with only a slight decrease in |Z| and increase in phase angle, implying that the Ni-MOF-74 is less resistive than the bare IDE. Upon exposure to humid $NO_2+SO_2+CO_2$, a transition to a resistive response is observed: |Z| plateaus to near 0.8 GΩ for frequencies <100 Hz, while the phase angle shifts to 0°. In order to extract the DC resistance, $R_{MOF}$, of Ni-MOF-74, the data were fit with an equivalent circuit shown in FIG. 3. This equivalent circuit is similar to that described in U.S. Pat. No. 11,573,217, except that it contains another constant phase element (CPE) to account for changes in the background capacitance of the measurement setup when humidity is introduced. See L. J. Small et al., *Adv. Funct. Mater.* 30, 2006598 (2020); L. J. Small and T. M. Nenoff, *ACS Appl. Mater. Interfaces* 9, 44649 (2017); L. J. Small et al., *ACS Appl. Mater. Interfaces* 11, 27982 (2019). The resulting fits are overlaid for the example spectra in FIGS. 2A and 2B. Across all fits, the goodness of fit, as judged by $\chi^2$, was better than 0.0059. Uncertainty of fitting individual circuit elements was small (<5%), less than sample-to-sample variability.

To verify that these changes in impedance were due to the Ni-MOF-74, several control experiments were performed. First, an uncoated IDE was activated and tested under each of the dry gases; no single gas or combination gave any response from the uncoated IDE. Thus, it is concluded that any observed electrical responses under dry conditions are due to changes in the electrical properties of the Ni-MOF-74, and not the underlying IDE. Under humid conditions, however, 1.56×, 2.60×, and 2.39× changes were observed in response to "humid $N_2$," "humid $NO_2$," and "humid $NO_2+SO_2+CO_2$," respectively. This result is not surprising; as water vapor condenses on the IDE's glass surface and gas species dissolve into it, the surface resistance across the glass IDE is expected to decrease. It is not possible to fit these differences to $R_{glass}$, which is fixed from measurements of the dry IDE before MOF deposition, to spectra which also have Ni-MOF-74. From this control experiment, it is concluded that small changes in $R_{MOF}$ under humid conditions may be due to changes in the underlying IDE. The large, three orders of magnitude change in impedance in FIG. 2A, however, cannot be solely attributed to changes in the IDE; it must be due to the Ni-MOF-74.

Figure 4:
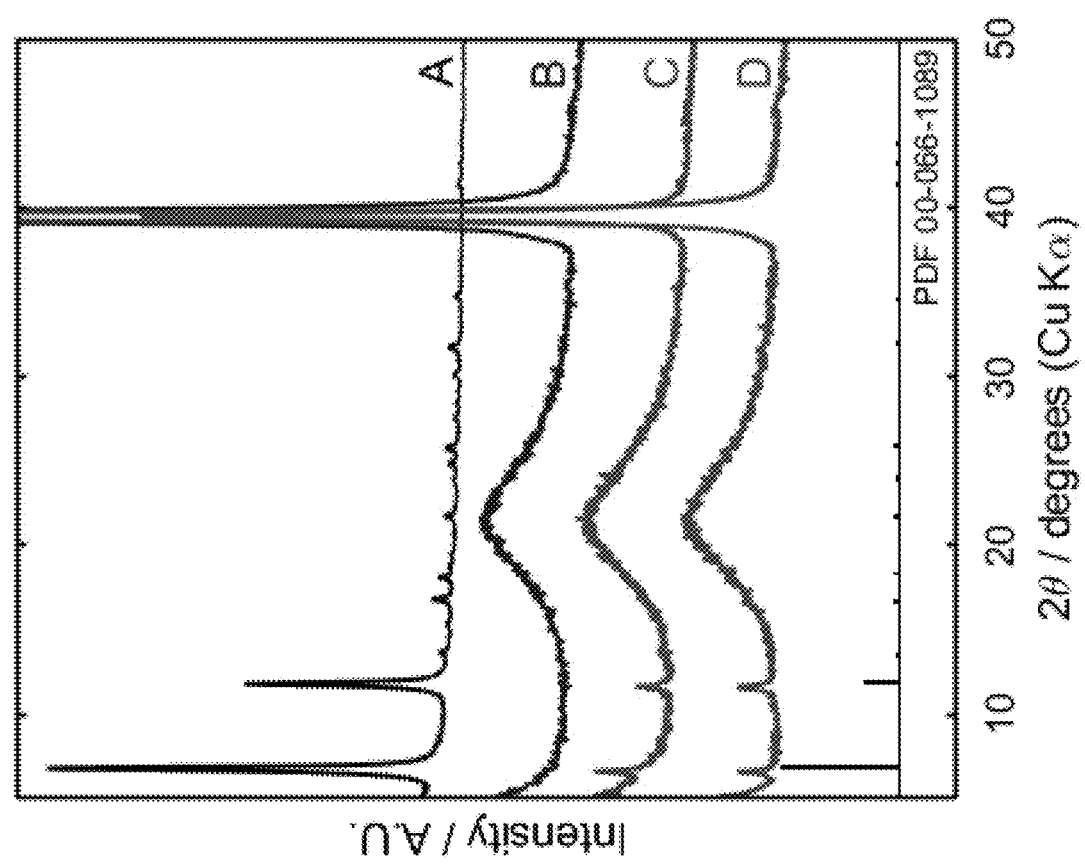
FIG. 4 is a plot of powder X-ray diffraction patterns of (A) Ni-MOF-74 bulk powder, (B) blank IDE, (C) Ni-MOF-74 coated IDE, and (D) Ni-MOF-74 coated IDE exposed to humid $NO_2+SO_2+CO_2$ for 5 h. PDF 00-066-1089 of Ni-MOF-74 is provided for comparison.

To verify that the Ni-MOF-74 structure was maintained after gas exposure, PXRD was performed on all samples and select data are plotted in FIG. 4. Here the as-synthesized Ni-MOF-74 powder (plot A) displays all major peaks expected from the reference pattern. Upon dropcasting Ni-MOF-74 onto the IDE (plot C), a broad peak at 22° associated with the glass substrate is seen, in addition to a sharp Pt(111) peak near 40° attributed to the Pt lines on the IDE (plot B). The Ni-MOF-74 peak intensity is suppressed due to low loading (1.21 mg), but major peaks near 6.9° and 12° are still readily identified. After exposure to humid $NO_2+SO_2+CO_2$, no appreciable change in PXRD is observed (plot D). Across all gas combinations, no significant changes in PXRD pattern were observed, implying structural stability of Ni-MOF-74 across all gas combinations and consistent with other literature reports. See L. J. Small et al., *Adv. Funct. Mater.* 30, 2006598 (2020).

FT-IR corroborated adsorption of each of the tested gases (except $N_2$) by Ni-MOF-74. From this complementary set of characterizations, it is inferred that the adsorption of the gas molecules by the stable Ni-MOF-74 structure altered the electrical properties of the MOF, creating the observed changes in electrical response.

Competing Gases Alter the Ni-MOF-74 Electrical Response

To compare the influence of the competitive gas environment on the electrical response of Ni-MOF-74, impedance spectra from all Ni-MOF-74 sensors (N=59) under all 16 gas conditions were fitted before and after gas exposure, and $R_{MOF}$ and $C_{MOF}$ were extracted for each. The ratio of $R_{MOF}$ before gas exposure to that after gas exposure is plotted in FIG. 5 for each gas combination.

Figure 5:
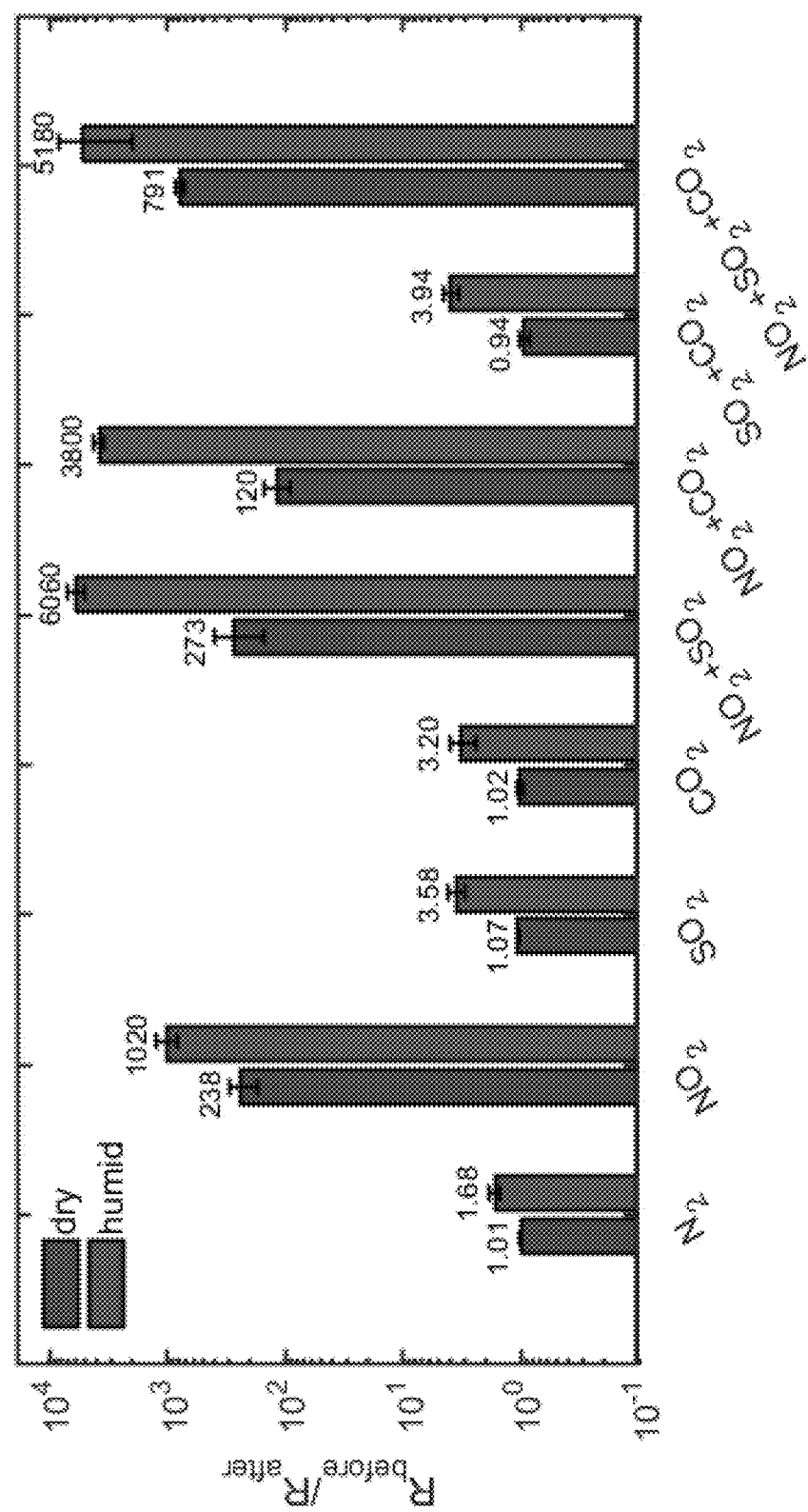
FIG. 5 is a graph showing a comparison of change in $R_{MOF}$ before gas exposure to that after gas exposure ($R_{before}/R_{after}$) for each gas combination from Table 1.

From FIG. 5, it is readily seen that the presence of $NO_2$ is necessary to achieve multiple orders of magnitude decrease in $R_{MOF}$, in excess of 6,000× in some cases. Gas combinations which do not contain $NO_2$ display significantly smaller decreases, all less than 4×. No statistically significant change was observed for dry $N_2$ or dry $CO_2$. A small change (1.07±0.03) was seen from dry $SO_2$, but this response was quenched for $SO_2+CO_2$ (0.94±0.08). Upon adding 0.8% humidity, the baseline $N_2$ response increased to 1.68±0.19, though much of this change can be attributed to the IDE alone (1.56) and may not represent any appreciable contribution from the MOF film. The humid $SO_2$, $CO_2$, and $SO_2+CO_2$ responses (3.58, 3.20, 3.94) are slightly higher than those observed for a blank IDE exposed to humid $NO_2$ (2.60) or humid $NO_2+SO_2+CO_2$ (2.39). It is hypothesized that the slightly increased response is due to the Ni-MOF-74 powder providing more exterior surface area for electrically conductive gas-laden $H_2O$ to be adsorbed and decrease the resistance across the bulk Ni-MOF-74 powder, as compared to the bare IDE.

Once $NO_2$ is added to the gas mixture, a large change in $R_{MOF}$ is observed. Under dry conditions this change is 238±63, increasing to 1020±220 under 0.8% humidity. Adding $SO_2$ to dry $NO_2$ has no appreciable effect on $R_{MOF}$, while adding $CO_2$ hinders the ability of $NO_2$ to change $R_{MOF}$. Remarkably, when added together, $SO_2$ and $CO_2$ enhance the dry $NO_2$ response, and under humid conditions enhance the response individually or combined, leading to the largest observed changes in $R_{MOF}$. Moreover, all competing gases tested, except dry $CO_2$, enhance the $NO_2$ response of the Ni-MOF-74 compared to dry $N_2$.

Figure 6:
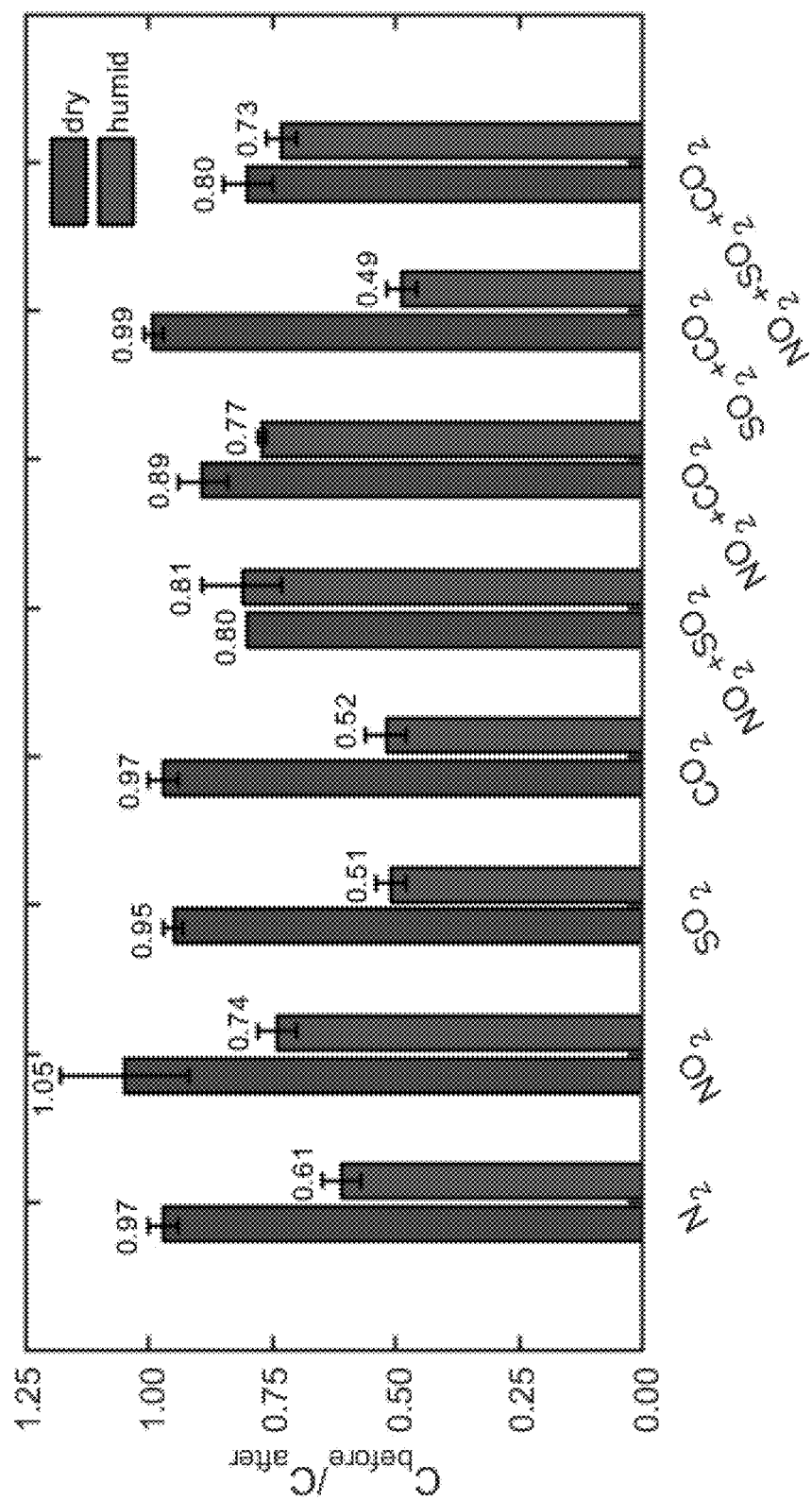
FIG. 6 is a graph showing a comparison of change in $C_{MOF}$ before gas exposure to that after gas exposure ($C_{before}/C_{after}$) for each gas stream.

Evaluating the capacitance of the MOF thin film, $C_{MOF}$, provides even more insight, and the ratio of $C_{MOF}$ before gas exposure to that after gas exposure is plotted in FIG. 6. These changes in capacitance provide a convenient method by which to classify the gas combinations as either (1) nonresponsive gases ($N_2$, $SO_2$, $CO_2$) or dry $NO_2$ ($C_{before}/C_{after}$=1.0×), (2) humid, no $NO_2$ ($C_{before}/C_{after}$=0.5-0.6×), or (3) $NO_2$+ other gases ($C_{before}/C_{after}$=0.7-0.9×), where humidity ($H_2O$) is included as "another gas." These results suggest that there is a significant interaction between the different adsorbed gas molecules in the MOF, increasing the capacitance after adsorption ($C_{before}/C_{after}$<1.0×). The nonresponsive gases ($SO_2$, $CO_2$), creating no change themselves, alter the capacitive response when added with $NO_2$. $NO_2$ appears to moderate the changes in capacitance created by $H_2O$. Interestingly, the change created by dry $NO_2+SO_2$ appears similar to that of humid $NO_2+SO_2$, while dry $NO_2+CO_2$ has a lesser effect.

Together, the resistance and capacitance values can be used to differentiate the effects of $NO_2$ and $H_2O$. If there is a large change in $R_{MOF}$ ($R_{after}/R_{before}$>4×), then $NO_2$ must be present. If there is no additional change in $C_{MOF}$, then $H_2O$ is absent. However, if the change in $R_{MOF}$ is accompanied by an moderate change in $C_{MOF}$ (0.7<$C_{before}/C_{after}$<0.9), then $H_2O$ is also present.

Real-Time Sensor Response Reveals Gas Competition

Figure 7A:
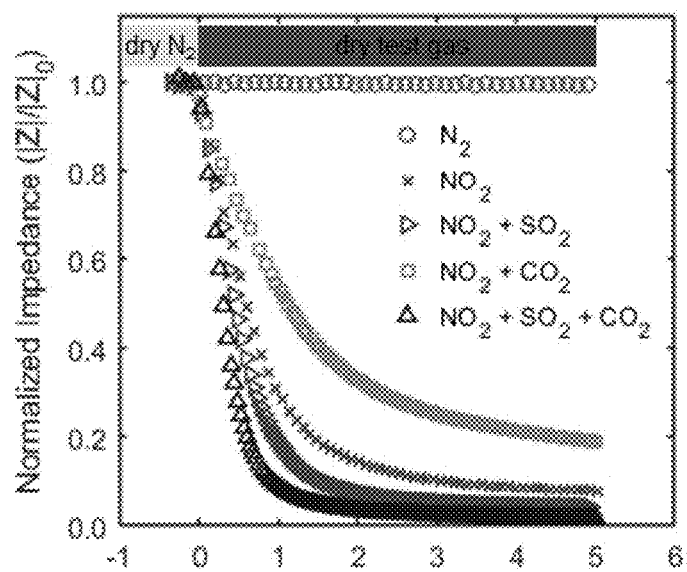
FIGS. 7A-C show real-time impedance measurements recorded at 100 mHz before and during gas exposure.

The changes in electrical properties of Ni-MOF-74 discussed above are after 5 h of gas exposure, sufficient time for the Ni-MOF-74 to equilibrate with the gas environment. To better understand how competitive gas adsorption influences the transient electrical response, impedance measurements at 100 mHz were continuously recorded during these gas exposures and the resulting data is plotted in FIG. 7A, comparing the $NO_2$-containing gas combinations to the $N_2$ control. Here the data has been normalized by the initial impedance magnitude ($|Z|_0$) to enable more meaningful comparison between samples. For all dry gas combinations, a constant impedance is initially recorded under dry $N_2$ flow. Once the $NO_2$-containing dry gas combination is introduced, an exponential decay in impedance magnitude is observed, consistent with previous results for a zeolite-based $NO_2$ sensor. See S. J. Percival et al., *Ind. Eng. Chem. Res.* 60, 14371 (2021). In this previous work, the exponential decay was related to the consumption of adsorption sites via chemical reaction kinetics of the first order. A single exponential decay from an initial ($|Z|_0$) to final ($|Z|_f$) can be approximated as follows:

$$|Z(t)|=(|Z|_0-|Z|_f)e^{-t/\tau}+|Z|_f \qquad (1)$$

Here $|Z(t)|$ is the impedance magnitude as a function of time (t), and $\tau$ is the time constant of the decay. The data in FIG. 7A was normalized by $|Z|_0$, and can be linearized as follows, enabling extraction of $\tau$.

$$\frac{|Z(t)|}{|Z|_0}=\left(\frac{|Z|_0-|Z|_f}{|Z|_0}\right)e^{-t/\tau}+\frac{|Z|_f}{|Z|_0} \qquad (2)$$

$$\frac{|Z(t)|-|Z|_f}{|Z|_0}=\left(\frac{|Z|_0-|Z|_f}{|Z|_0}\right)e^{-t/\tau} \qquad (3)$$

$$\ln\left(\frac{|Z(t)|-|Z|_f}{|Z|_0}\right)=\frac{-t}{\tau}+\ln\left(\frac{|Z|_0-|Z|_f}{|Z|_0}\right) \qquad (4)$$

Figure 7B:
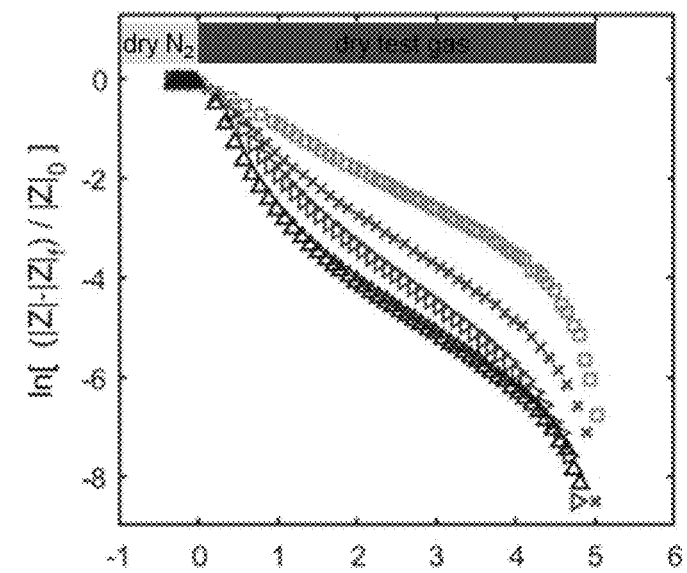

A plot of ln $$\left(\frac{|Z(t)|-|Z|_f}{|Z|_0}\right)$$

versus time is shown in FIG. 7B. For dry $NO_2$, dry $NO_2+SO_2$, and dry $NO_2+SO_2+CO_2$, two distinct slopes are seen: a steeper slope (smaller $\tau$) during the first hour, followed by a shallower slope (larger $\tau$) over hours 1-4. The final slope (t>4 h) is an artifact of the analysis; an ideal exponential decay will approach, but never obtain its final value, whereas here $|Z|_f$ was approximated as the value after 5 h. From this data, it is inferred that Ni-MOF-74 exposed to dry $NO_2$, dry $NO_2+SO_2$, or dry $NO_2+SO_2+CO_2$ displays two distinct processes that contribute to the decrease in impedance: a fast initial process, and a slower second process. Similar results have been seen for the impedance change of Ni-SSZ-13 zeolite exposed to trace $NO_2$, where the different processes were attributed to $NO_2$ adsorbed on the crystallite exterior surfaces (faster) and interior surfaces (slower). See S. J. Percival et al., *Ind. Eng. Chem. Res.* 60, 14371 (2021).

In contrast, Ni-MOF-74 exposed to dry $NO_2+CO_2$ exhibits a constant slope over the first 4 h of exposure, indicating a single time constant and one process. Moreover, this single process is similar in slope (time constant) to the slower process of the other $NO_2$-containing gas combinations. This suggests that $CO_2$ interferes with the fast $NO_2$ adsorption process. This effect is not simply due to differences in concentration of $NO_2$ (1 ppm) and $CO_2$ (100,000 ppm), as the addition of $SO_2$ (1 ppm) reenables the fast $NO_2$ adsorption process. Under dry conditions, the displacement of $CO_2$ by $SO_2$ is likely more favorable than $CO_2$ by $NO_2$. This hypothesis is supported by the fact that $NO_2+CO_2$ displayed a smaller change in $R_{MOF}$ compared to $NO_2$; even after 5 h all of the electrically active adsorption sites occupied by $CO_2$ could not be displaced by $NO_2$.

Figure 7C:
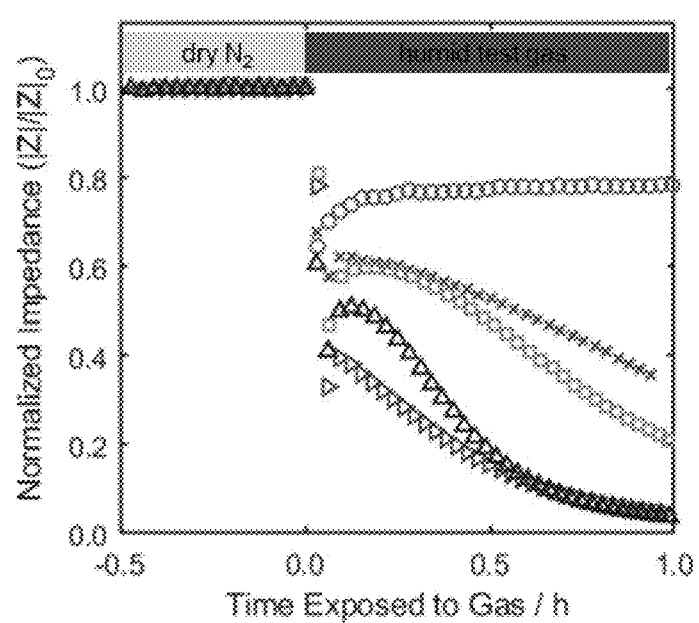

Addition of humidity ($H_2O$) to the gas combination creates a significant difference in the transient impedance response and can be related to the gases present and competing for the Ni-MOF-74 adsorption sites. This difference is most pronounced during the first hour and is plotted in FIG. 7C. During the initial exposure to dry $N_2$ all sensors display a constant $|Z|$. Upon exposure to the humid gas streams, a sharp decrease in $|Z|$ is immediately observed (<120 s), followed by a gradual increase in $|Z|$. This relatively fast diffusion and adsorption of $H_2O$ into MOF-74 films was observed via FT-IR by Tan et al. See K. Tan et al., *Chem. Mater.* 27, 2203 (2015). For humid $N_2$, this increase stabilizes to within 2.6% of the final value within the first 0.25 h. Clearly, $H_2O$ is rapidly adsorbed by Ni-MOF-74. For all $NO_2$-containing gas combinations, this increase is short-lived and $|Z|$ gradually decreases again. Gas combinations containing $CO_2$ required a longer time to finally decrease in $|Z|$, consistent with the dry case, where $CO_2$ interfered with $NO_2$ adsorption. Likewise, humid $NO_2+SO_2+CO_2$ was faster to recover than humid $NO_2+CO_2$ was, consistent with the observation in the dry case the $SO_2$ moderates $CO_2$'s deleterious effects on $NO_2$ adsorption.

At times >1 h, a plot of ln $$\left(\frac{|Z(t)|-|Z|_f}{|Z|_0}\right)$$

versus time yields a constant slope for humid $NO_2$, suggesting a single adsorption process analogous to the dry cases. This process is likely the displacement of the quickly adsorbed $H_2O$ by much slower $NO_2$. Addition of other gases, however, creates curves which are not simply described by a linear fit. This suggests a more complex interplay between the competing gases under humid conditions as an equilibrium adsorption configuration is gradually achieved across all MOF adsorption sites.

In sum, changes in the transient impedance response may be attributed to the adsorption and exchange of the competing gases. The adsorption of $NO_2$ is the driver for the large decrease in impedance observed. Co-adsorption of $CO_2$ hinders the kinetics of this process, though it can be moderated by the addition of $SO_2$. The adsorption of $H_2O$ is much faster than that of $NO_2$, and the adsorption of $NO_2$ in the $H_2O$ saturated Ni-MOF-74 is further hindered by $CO_2$.

Ni-MOF-74: Gas Selectivity

It is important to understand how the various gases might interact with Ni-MOF-74 during $H_2O$ detection. $H_2O$, $N_2O$, and $CO_2$ are known to be adsorbed by M-MOF-74. These gases and $SO_2$, also adsorbed by M-MOF-74, are often present in environments containing industrial flue gases.

The source of this selective electrical response is believed to be related to the relative electronic structures of the Ni-MOF-74 and the competing gas species. While many different gas molecules will readily adsorb to the unsaturated metal sites in Ni-MOF-74, a large change in $R_{MOF}$ is only expected if there is a significant amount of MOF-adsorbate electron transfer, creating new unoccupied electron states that facilitate charge transport in Ni-MOF-74. Thus, adsorption of triply bound $N_2$, with its tightly held electrons, is not expected to influence $R_{MOF}$.

On the other hand, $NO_2$ is a radical molecule that can serve as both an electron acceptor and donor. The $NO_2$ highest occupied molecular orbital (HOMO) and lowest unoccupied molecular orbital (LUMO) sits below the Ni-MOF-74's HOMO, which contains significant contributions from Ni electrons. See K. Tan et al., *Chem. Mater.* 29, 4227 (2017); L. Sun et al., *Chem Sci.* 8, 4450 (2017); and J. A. Rodriquez et al., *J. Mol. Catal. A: Chem.* 167, 47 (2001). Electrons from the Ni-MOF-74 HOMO may be transferred to the $NO_2$ LUMO, creating newly reorganized unoccupied states in Ni-MOF-74, facilitating electronic transport, and decreasing $R_{MOF}$.

Compared to $NO_2$, $SO_2$ displays a LUMO at energy levels much closer to vacuum level. See K. Tan et al., *Chem. Mater.* 29, 4227 (2017); and J. A. Rodriquez et al., *J. Mol. Catal. A: Chem.* 167, 47 (2001). This significantly impedes electron transfer; reports have suggested that $SO_2$ adsorption in M-MOF-74 is more akin to physisorption than chemisorption. See K. Tan et al., *Chem. Mater.* 29, 4227 (2017). Therefore, no significant change in $R_{MOF}$ is expected upon adsorption of $SO_2$.

Likewise, significant charge transfer is not expected for $CO_2$ due to relative band locations. Moreover, studies on the competitive adsorption of $CO_2$ and $H_2O$ suggest that $CO_2$ is preferentially exchanged for $H_2O$, making significant adsorption of $CO_2$ from air unlikely.

Interactions with $H_2O$ are more complex. The LUMO of water sits above Ni-MOF-74's HOMO; significant electron transfer is not expected, consistent with reports of molecularly adsorbed $H_2O$, and no dissociation. Nevertheless, high binding energy of $H_2O$, only slightly less than that of $NO_2$, indicates a strong interaction with the metal center. See K. Tan et al., *Chem. Mater.* 27, 2203 (2015). Calculations have predicted that the decreased electron density on a Zn-MOF-74 metal center leads to an decrease in effective mass for Zn-MOF-74 electrons. See P. Canepa et al., *J. Mater. Chem. A* 3, 986 (2015). As effective mass is theoretically proportional to resistivity, a similar decrease in $R_{MOF}$ is expected and observed.

The present invention has been described as low power mixed gas sensor. It will be understood that the above description is merely illustrative of the applications of the principles of the present invention, the scope of which is to be determined by the claims viewed in light of the specification. Other variants and modifications of the invention will be apparent to those of skill in the art.

We claim:

1. A low power mixed gas sensor, comprising:
   an electrically insulating substrate;
   a pair of interdigitated electrodes disposed on the substrate;
   a mixed-gas-capture film that absorbs two or more target gases in a multi-gas environment, wherein the mixed-gas-capture film comprises a metal-organic framework material disposed on the pair of interdigitated electrodes and the substrate, and wherein the metal-organic framework (MOF) material comprises M-MOF-74, wherein M is cobalt, magnesium, zinc, or nickel, or RE-DOBDC, where RE is a rare-earth element and DOBDC is dihydroxyterephthalic acid; and a frequency response analyzer configured to measure the impedance response of the mixed-gas-capture film when the two or more target gases are absorbed in the mixed-gas-capture film and an alternating voltage is applied to the pair of interdigitated electrodes.

2. The sensor of claim 1, wherein the mixed-gas-capture film has a thickness of less than 100 μm.

3. The sensor of claim 2, wherein the mixed-gas-capture film has a thickness of less than 10 μm.

4. The sensor of claim 1, wherein the substrate comprises a silica glass substrate.

5. The sensor of claim 1, wherein the alternating voltage has a frequency between 1 mHz and 1 MHz.

6. The sensor of claim 1, further comprising a high impedance interface connected in series with the frequency response analyzer.

7. The sensor of claim 1, wherein the mixed-gas-capture film absorbs the two or more target gases comprising $NO_x$, $SO_x$, $CO_x$, and $H_2O$ from the multi-gas environment.

8. A method for detecting individual gases in a mixed gas stream, comprising:
  providing a low power mixed gas sensor, comprising:
    an electrically insulating substrate,
    a pair interdigitated electrodes disposed on the substrate;
    a mixed-gas-capture film that absorbs two or more target gases in a multi-gas environment, when the mixed-gas-capture film comprises a metal-organic framework material disposed on the pair of interdigitated electrodes and the substrate, and wherein the metal-organic framework (MOF) material comprises M-MOF-74, wherein M is cobalt, magnesium, zinc or nickel, or RE-DOBDC, where RE is a rare-earth element and DOBDC is dihydroxyterephthalic acid; and
  a frequency response analyzer configured to measure the impedance response of the mixed-gas-capture film when the two or more target gases are absorbed in the mixed-gas-capture film and an alternating voltage is applied to the pair of interdigitated electrodes; exposing the mixed gas sensor to a mixed gas stream; and measuring the impedance response of the mixed-gas-capture film.

9. The method of claim 8, wherein the step of exposing comprises exposure to the mixed gas stream for a sufficient time for the mixed-gas-capture film to equilibrate with the mixed gas stream, so that the measuring step provides a steady state impedance response.

10. The method of claim 8, wherein the measuring step provides a transient impedance response.

11. The method of claim 8, wherein the mixed-gas-capture film absorbs the two or more target gases comprising $NO_x$, $SO_x$, $CO_x$, and $H_2O$ from the multi-gas environment.

* * * * *